United States Patent [19]
Lloyd et al.

[11] Patent Number: 5,281,287
[45] Date of Patent: Jan. 25, 1994

[54] METHOD OF MAKING A HYDRATABLE BIOELECTRODE

[75] Inventors: Lindsay B. Lloyd, West Jordan; Jon E. Beck, Salt Lake City; Tomasz J. Petelenz, Salt Lake City; Stephen C. Jacobsen, Salt Lake City, all of Utah

[73] Assignee: Iomed, Inc., Salt Lake City, Utah

[21] Appl. No.: 31,260

[22] Filed: Mar. 12, 1993

Related U.S. Application Data

[60] Division of Ser. No. 627,714, Dec. 14, 1990, Pat. No. 5,236,412, which is a continuation-in-part of Ser. No. 383,939, Jul. 21, 1989, Pat. No. 5,087,242.

[51] Int. Cl.$^5$ .............................................. A61N 1/30
[52] U.S. Cl. ......................................... 156/80; 156/83; 156/250; 156/292; 156/284; 156/305; 604/20; 607/149; 204/400
[58] Field of Search ................... 604/20; 204/400, 415; 607/149; 156/80, 83, 191, 230, 234, 247, 250, 269, 292, 284, 296, 305, 276

[56] References Cited

U.S. PATENT DOCUMENTS

| | | | |
|---|---|---|---|
| 3,998,215 | 12/1976 | Anderson et al. | 128/641 |
| 4,777,954 | 10/1988 | Keusch et al. | 128/641 |
| 4,921,475 | 5/1990 | Sibalis . | |
| 4,989,607 | 2/1991 | Keusch et al. | 128/640 |
| 5,087,242 | 2/1992 | Petelenz et al. | 604/20 |

Primary Examiner—Jeff H. Aftergut
Attorney, Agent, or Firm—Workman, Nydegger & Jensen

[57] ABSTRACT

A hydratable iontophoretic bioelectrode includes a plurality of layers of material capable of absorbing and holding an ionized fluid when placed in contact with the fluid. Adjacent layers are maintained at least partially out of contact from one another by disposition between the layers of spacing elements such as sugar or other dissolvable particles or cellulose. The edges of the layers may be crimped to maintain the layers in a stack for assembly with an electrode sheet; such a sheet would be provided for receiving an electrical current to thereby produce an electric field and cause a migration of ions of the ionized fluid away from the electrode sheet and into the skin or tissue of a person or animal against which the bioelectrode is placed.

14 Claims, 3 Drawing Sheets

METHOD OF MAKING A HYDRATABLE BIOELECTRODE

This application is a divisional of application Ser. No. 07/627,714, filed Dec. 14, 1990, now U.S. Pat. No. 5,236,412 which is a continuation-in-part application of application Ser. No. 383,939, filed Jul. 21, 1989, now U.S. Pat. No. 5,087,242.

BACKGROUND OF THE INVENTION

This invention relates to a rehydratable product or membrane especially suitable for use in an iontophoretic bioelectrode system, and to a method of preparing the rehydratable membrane.

Iontophoretic bioelectrodes, used in place of hypodermic needles to inject medications into a person's skin or tissue, typically include a pouch or similar enclosure formed with a wettable barrier or a microporous membrane on one side thereof. See, for example, U.S. Pat. Nos. 4,250,878, 4,419,092 and 4,477,971. A medication solution containing ions to be delivered into the person's skin or tissue is injected into the pouch by means of a hypodermic needle, syringe, etc. When the wettable barrier or membrane is placed against a person's skin and an electric current is supplied to the solution, the ions are caused to migrate from the solution through the wettable barrier or membrane, and into the skin.

A second bioelectrode is used in conjunction with the above-described iontophoretic bioelectrode, but does not include a solution of ions. Rather, the second bioelectrode need only include an element for making contact with the person's skin or tissue (generally in close proximity to the iontophoretic bioelectrode), such as a wettable barrier or membrane for allowing migration of current (of opposite polarity to that of the current supplied to the iontophoretic bioelectrode) between the person's skin or tissue through the contact element to a second current source.

For the iontophoretic bioelectrode described earlier, barriers or membranes are required to retain the solution in the pouch while allowing ions to migrate therethrough. However, such barriers or membranes also inhibit wetting of the skin and thus inhibit the migration of ions to a certain extent, at least as compared to a situation where the solution were in direct contact with the skin. Also, because of the use of a pouch or similar enclosure to contain the medication solution, a mechanism or structure on the enclosure is necessary for allowing the injection thereinto of the solution. Such structure has typically included some type of orifice containing a plug into which a hypodermic needle or syringe tube may be inserted to allow delivery of the solution through the orifice into the interior of the enclosure, while preventing the outflow of the solution after it has been injected into the enclosure. The requirement of such solution receiving mechanism or enclosure, of course, increases the cost of the bioelectrode and gives rise to potential leakage locations.

In copending patent application, Ser. No. 383,939, a hydratable bioelectrode is disclosed in which the need for special solution receiving structure or mechanisms is obviated. This bioelectrode includes a layer of material for absorbing and holding aqueous solutions when placed in contact therewith, a conductive sheet disposed in close proximity to the layer of material for receiving an electrical charge to thereby cause ions in the fluid to move to and from the layer of material toward or away from the conductive sheet, and a support base on which the layer of material and conductive sheet are mounted. The layer of material may comprise a polymer, a matrix of fibers impregnated or interwoven with a hydratable polymer, or similar ion solution absorbing material. This bioelectrode structure provides a simple, inexpensive and easy to use iontophoretic delivery mechanism.

SUMMARY OF THE INVENTION

It is an object of the invention to provide a method and structure for a simple, inexpensive, and skin contour conformable iontophoretic bioelectrode.

It is also an object of the invention to provide such an iontophoretic bioelectrode capable of efficiently absorbing and holding an aqueous solution when placed in contact therewith.

It is an additional object of the invention to provide such an iontophoretic bioelectrode which may be constructed using conventional equipment.

The above and other objects of the invention are realized in a specific illustrative embodiment of a hydratable bioelectrode for delivering medicament into the skin or tissue of a person or animal, where the medicament is ionized. The bioelectrode includes a hydratable element for absorbing ionized medicament in aqueous solution when placed in contact therewith, apparatus for holding the hydratable element, and an electrode mounted on the holding apparatus in proximity to the hydratable element for receiving an electrical current to thereby produce an electrical field and cause ionized medicament to move from the hydratable element into the skin or tissue on which the bioelectrode is placed. The hydratable element, in turn, includes a stack of at least two sheets of hydrogel for absorbing medicament, separating elements for maintaining adjacent sheets at least partially separated, and structure for holding the sheets in the stack. An alternative to use of separating elements would be to form fluid channels between the sheets.

In accordance with one aspect of the invention, the separation elements are comprised of granules or fibers disposed between each pair of adjacent sheets of hydrogel, with such granules or fibers comprising, for example, sugar crystals, cellulose fibers, etc.

In accordance with another aspect of the invention, the sheets of hydrogel are formed to be relatively stiff to enable maintaining the sheets apart from one another by the separation elements so that when the sheets are exposed to medicament for absorbtion thereof, there is a greater surface area of the hydrogel sheets in contact with the medicament and thus there is a more rapid complete and uniform absorbtion.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1A:
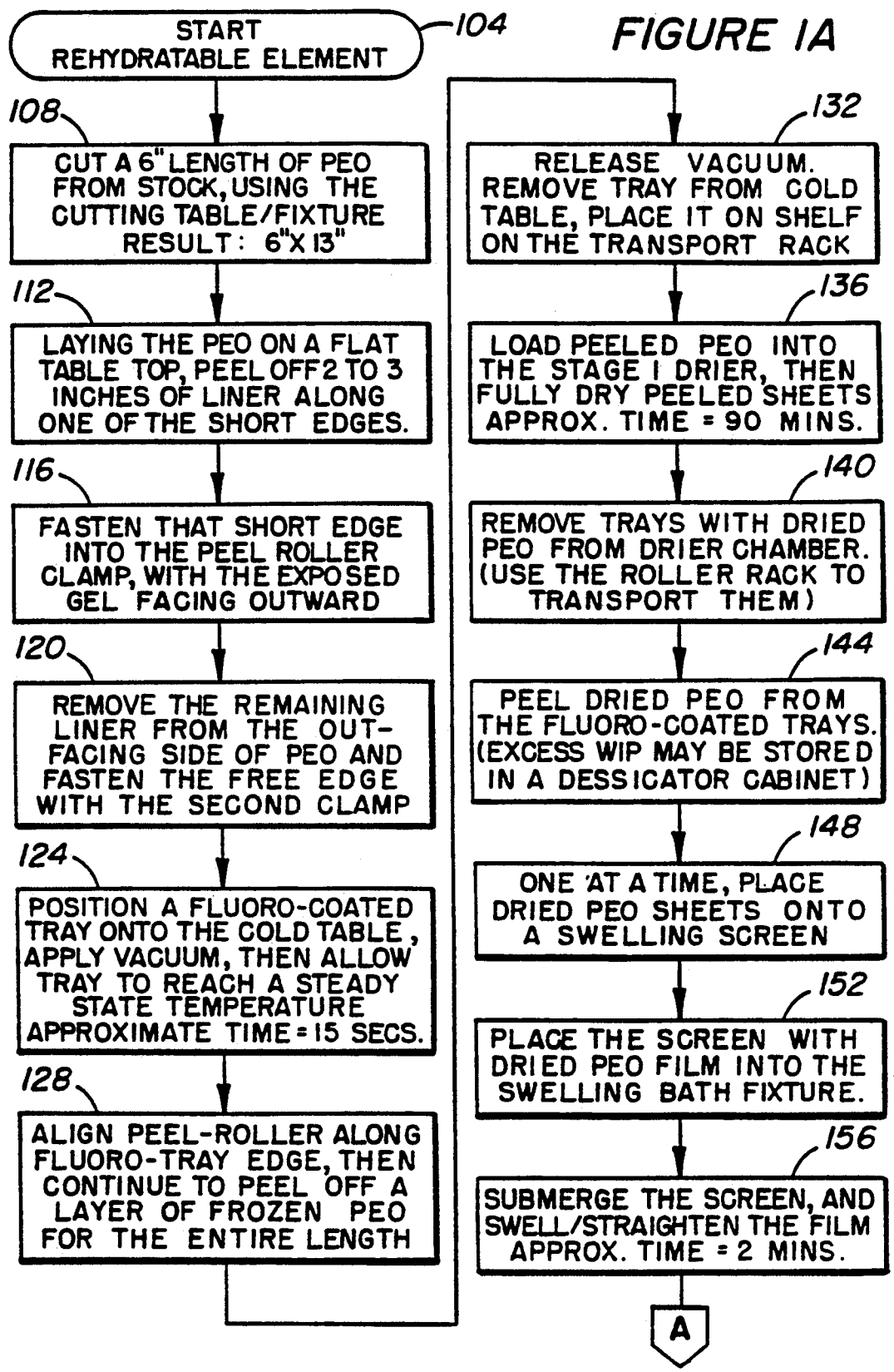
FIGS. 1A and 1B show a flow diagram of a method of constructing hydratable bioelectrodes in accordance with the principles of the present invention.
Figure 1B:
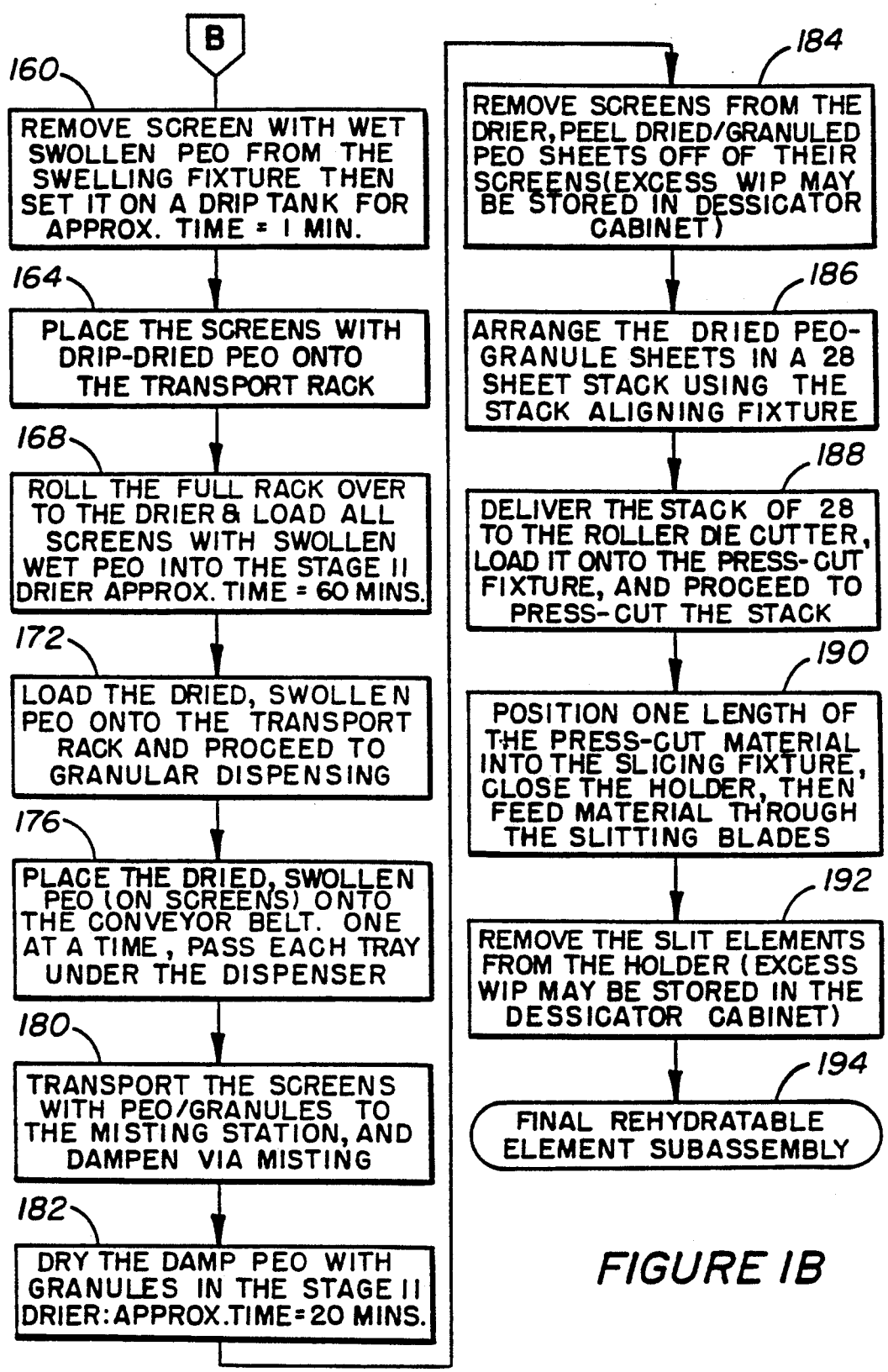

FIGS. 1A and 1B are a flow chart showing the steps of one embodiment of a method of producing a hydratable bioelectrode in accordance with the present invention. An exemplary starting material for the method of FIGS. 1A and 1B are shown in cross section in FIG. 2 to include a mass of gel material 204 sandwiched between two layers of liner material 208 and 212 made, for example, of plastic. A sheet of scrim (mesh material) 216 is disposed in the gel mass generally midway between the two liners 208 and 212. The starting material illustrated in FIG. 2 might illustratively be an inert hydrogel identified as STD-1 or WD-1 which are the products of Nepera, Inc. used as a skin dressing for wounds, burns, etc. These particular hydrogels constitute a polyethylene oxide polymer which is crosslinked, for example, using e-beam radiation, by chemical means, or by other strong radiation such as gamma rays. The starting material could also be a polyacrylamide polymer, copolymer, or other polymer capable of absorbing water.

Figure 2:
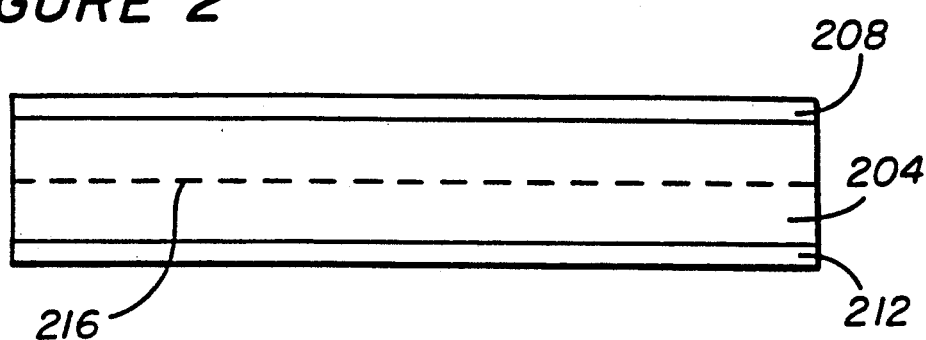
FIG. 2 shows a side, cross-sectional view of a starting product for use in the method illustrated in FIG. 1.

Referring now to FIG. 1A, the first step of the method or process of producing a hydratable bioelectrode is to provide a starting material such as that shown in FIG. 2. From such a stock piece of material, a strip of, for example, six inches by thirteen inches is cut out in a conventional fashion (step 108 of FIG. 1) and then laid flat on a table to allow peeling off of the top liner sheet 208 (steps 112, 116 and 120 of FIG. 1A). (The term "PEO" used in some of the steps of FIGS. 1A and 1B means "polyethylene oxide", and the term "WIP" means "work in process".) Although the steps shown in boxes 112, 116 and 120 of FIG. 1A are rather specific for peeling off the top liner 208 of the starting material of FIG. 2, it should be understood that any of a variety of approaches could be taken for removing the liner; further starting material without any liner to begin with could be provided and then, of course, steps 112, 116 and 120 would not be necessary.

After step 120 of FIG. 1A, the gel mass or layer 204 and remaining liner 212 are wound about a roller device so that the gel layer 204 faces outwardly. The next step in the process is to place a fluoroplastic-coated tray onto a cold table to cool the tray, with the tray being held in place by a vacuum in a conventional fashion. When the tray reaches a steady state temperature of, for example, eighteen degrees Fahrenheit (a temperature below the freezing point of the gel layer), as indicated in step 124, the roller, with gel layer wound thereabout, is aligned along one edge of the cooled tray (step 128) and rolled at a predetermined, controlled rate to cause the outward facing or upper layer of the gel material 204 to freeze and hold onto the tray so that as the roller continues to roll, the thin upper layer (down to the scrim 216) is peeled away from the remainder of the gel on the roller and frozen onto the tray. If no scrim 216 were present in the gel mass 204, the tray temperature, and rate of rolling the roller, would determine the thickness of the layer of gel which is frozen to the tray and peeled from the roller. A layer of gel is now disposed on the tray and another gel layer sandwiched between the scrim 216 and liner 212 remains on the roller.

With the layer of gel on the tray, the tray is placed in a convection drying chamber (step 136) which has been heated to about 55° centigrade. The purpose of this is to dry the gel layer at a temperature which will not cause degradation of the gel (typically about 60° centigrade). The dried gel layer is then removed from the tray and placed onto a screen and clamped to maintain the planarity of the layer (steps 144 and 148), and the screen is then immersed in a "swelling" solution of water (step 152) containing a stiffening agent such as sugar, for example, 50 grams per liter. The purpose of the stiffening agent will be discussed later. The screen on which the gel layer is placed may illustratively be a perforated fluoro-coated metal sheet, with another screen on top to maintain the flatness of the gel layer.

The screen with gel layer remains submerged in the swelling solution for a sufficient time to allow the layer to absorb solution, swell and expand laterally (step 156). The screen with swollen gel layer is then removed from the swelling solution, blotted dry (step 160) and after sufficient blotting, the screen with gel layer is again placed in the convection drying chamber to further dry the gel layer (step 168). After swelling and the final step of drying, the gel layer will have substantially the same length and width dimensions, but the thickness will have decreased substantially from when wet.

In the next stage of the process, granules or fibers are distributed onto the gel layer to serve as spacers to maintain apart, to the extent possible, adjacent gel layers which will later be used to form a stack of gel layers. Individual gel layers will be fairly stiff, as a result of immersion thereof in the swelling solution with stiffening agent, and so the distribution of granules or fibers, such as sugar or salt crystals or cellulose, over the gel layers will serve as spacers when the gel layers are placed in a stack. One way of distributing the granules or fibers onto the gel layer is to place the gel layer onto a conveyor belt and pass it under a granule/fiber dispenser (step 176). It is desired to maintain individual gel layers separated when in a stack so that when hydrated with iontophoretic medicament, the medicament will be allowed to flow between the layers and thus be more rapidly and uniformly absorbed by the ultimate gel layer stack.

In step 180, a fine water vapor or mist is applied to the gel layer simply to better hold the granules or fibers on the gel layer surface. The water vapor or mist partially dissolves granules such as sugar causing them to "stick" onto the gel layer. It is important that too much water vapor or mist not be used so that the granules are not dissolved completely, since, of course, they would then not serve to maintain the gel layer separated from adjacent layers.

After securing the granules or fibers onto the gel layer, the gel layer is removed from the screen (step 184) and then arranged in a stack with other gel layers, for a total, for example, of 28 layers (step 186). A sufficient number of gel layers are included in a stack so that when the gel layers are incorporated into a bioelectrode such as that shown in FIG. 3, the electrode sheet 304 which receives electrical current from a current source 308 will not burn the skin or tissue of a person against which the bioelectrode is placed. On the other hand, if too many layers are used to form the stack, then assembly may become too costly.

Figure 3:
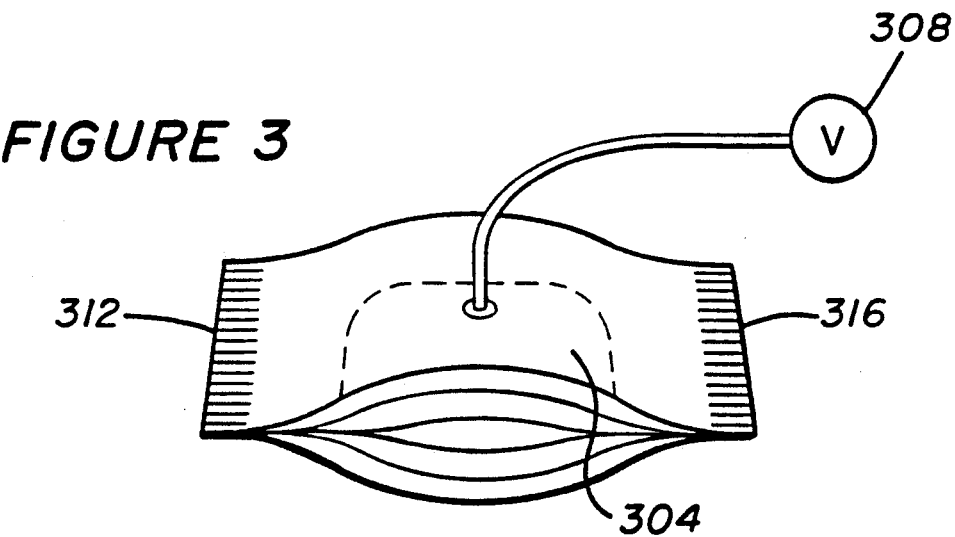
FIG. 3 is an end, cross-sectional view of an iontophoretic bioelectrode made in accordance with the principles of the present invention.

After the layers are formed into a stack, the stack is press-cut by a roller press (step 188) which both cuts the stack lengthwise, for example, and also crimps the resulting adjacent edges so cut. FIG. 3 shows opposite edges 312 and 316 of a gel layer stack which have been crimped and cut. Note that the edges which are crimped are much thinner than the center portion of the stack which, of course, has not been crimped. In step 190, the stack is then cut perpendicularly to the press-cut made in step 188 to thereby provide a plurality of individual stacks of gel layers, each of which may then be incorporated into a bioelectrode structure such as that shown in FIG. 3 (step 194 of FIG. 1B).

In the manner described, a simple iontophoretic bioelectrode is provided in which the ionized medicament may be absorbed into a stack of gel layers which are part of the bioelectrode. The hydratable layers may then be placed in direct contact with the skin or tissue of a person or animal for administering the medicament and because the gel layers are in direct contact, improved wetting of the skin or tissue, and thus more efficient delivery of the ions, is achieved.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A method of producing a hydratable bioelectrode from a mass of hydrogel comprising the steps of
   (a) forming the mass of hydrogel into sheets of hydrogel,
   (b) drying the sheets of hydrogel,
   (c) disposing the dried sheets in a swelling solution to cause the sheets to absorb solution, swell and expand laterally,
   (d) drying the sheets of swollen hydrogel,
   (e) distributing granules/fibers onto the sheets, and
   (f) arranging the sheets into a stack where adjacent sheets are at least partially maintained apart by the granules/fibers.

2. A method as in claim 1 further comprising the step of
   (g) cutting the stack, from top to bottom, into two or more parts.

3. A method as in claim 1 wherein step (a) comprises
   (h) placing the mass of hydrogel on the exterior surface of a roller,
   (i) rolling the roller with hydrogel over the surface of a cooled tray to thereby cool an outer layer of gel as it contacts the tray, causing it to freeze superficially, adhere to the tray and pull away from the hydrogel mass remaining on the roller, thereby forming a sheet of hydrogel.

4. A method as in claim 3 wherein the tray is cooled to a temperature below the freezing point of the hydrogel.

5. A method as in claim 3 wherein the roller is rolled at a substantially constant rate.

6. A method as in claim 1 wherein step (b) comprises drying the sheets of hydrogel in a convection oven at an elevated temperature.

7. A method as in claim 6 wherein the convention oven is heated to a temperature of about 55° C.

8. A method as in claim 1 wherein step (c) comprises
   (j) placing the sheets of hydrogel on a screen, and
   (k) immersing the screen with hydrogel sheets in a solution of water and stiffening agent to cause the sheets to swell and ultimately stiffen.

9. A method as in claim 8 wherein the stiffening agent is sugar.

10. A method as in claim 1 wherein step (e) comprises
    (l) moving the sheets of hydrogel under a granule/fiber dispensing mechanism to deposit granules/fibers onto the sheets, and
    (m) applying water mist or vapor to the sheets and granules/fibers to moisten the granules/fibers to facilitate holding them in place on the sheets.

11. A method as in claim 10 wherein said granules/fibers are sugar crystals.

12. A method as in claim 2 wherein step (g) further comprises crimping together corresponding edges on opposite sides of the sheets.

13. A method as in claim 12 wherein step (g) further comprises crimping the resulting adjacent edges formed by the cutting.

14. A method as in claim 13 wherein step (g) comprises press-cutting the stack along one or more generally parallel first lines, and slicing the press-cut parts along lines generally perpendicular to the first lines.

* * * * *